United States Patent
Ehlenz et al.

(10) Patent No.: US 8,362,269 B2
(45) Date of Patent: Jan. 29, 2013

(54) PREPARATION OF 1,7'-DIMETHYL-2'-PROPYL-2,5'-BI-1H-BENZIMIDAZOLE

(75) Inventors: Richard Ehlenz, Bad Kreuznach (DE); Oliver Meyer, Dorsheim (DE); Hartmut Schmidt, Bockenau (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 9 days.

(21) Appl. No.: 12/989,522

(22) PCT Filed: Apr. 29, 2009

(86) PCT No.: PCT/EP2009/055162
§ 371 (c)(1),
(2), (4) Date: Jan. 6, 2011

(87) PCT Pub. No.: WO2009/133122
PCT Pub. Date: Nov. 5, 2009

(65) Prior Publication Data
US 2011/0190508 A1     Aug. 4, 2011

(30) Foreign Application Priority Data
May 2, 2008   (EP) ..................... 08155560

(51) Int. Cl.
*C07D 403/04*   (2006.01)
(52) U.S. Cl. .................................. 548/305.4
(58) Field of Classification Search ............... 548/305.4
See application file for complete search history.

(56) References Cited

U.S. PATENT DOCUMENTS

| 6,770,762 B2 | 8/2004 | Belzer et al. |
| 7,608,722 B2 * | 10/2009 | Heitger et al. ............. 548/305.4 |
| 2004/0225129 A1 | 11/2004 | Belzer et al. |

FOREIGN PATENT DOCUMENTS

| CA | 2471730 | * | 7/2003 |
| WO | 03/059890 A1 | | 7/2003 |
| WO | WO-2007/009967 A1 | * | 1/2007 |

OTHER PUBLICATIONS

International Search Report for PCT/EP2009/055162 mailed Aug. 4, 2009.

* cited by examiner

*Primary Examiner* — Laura L. Stockton
(74) *Attorney, Agent, or Firm* — Michael P. Morris; Timothy X. Witkowski

(57) ABSTRACT

The invention relates to a process for preparing 1,7'-dimethyl-2'-propyl-2,5'-bi-1H-benzimidazole of formula (I)

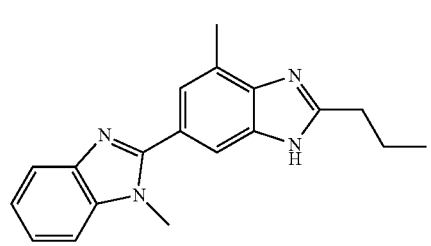

(I)

11 Claims, No Drawings

PREPARATION OF 1,7'-DIMETHYL-2'-PROPYL-2,5'-BI-1H-BENZIMIDAZOLE

This application is the national phase entry under 35 U.S.C. §371 of International Application No. PCT/EP2009/055162, filed Apr. 29, 2009, which claims priority to European Patent Application No. 08155560.9, filed May 2, 2008.

The invention relates to benzimidazoles substituted at position 2.

1,7'-dimethyl-2'-propyl-2,5'-bi-1H-benzimidazole is used as an intermediate product in the large-scale synthesis of telmisartan. Its use as a pharmaceutical active substance demands that the 1,7'-dimethyl-2'-propyl-2,5'-bi-1H-benzimidazole used for the synthesis has a very high degree of purity.

WO 03/059890 describes the preparation of 1,7'-dimethyl-2'-propyl-2,5'-bi-1H-benzimidazole by reacting 2-propyl-4-methyl-1H-benzimidazole-6-carboxylic acid with N-methyl-o-phenylene-diamine in the presence of methanesulphonic acid and phosphorus pentoxide. According to the process described therein, the starting materials N-methyl-o-phenylene-diamine of formula (II) or the salts thereof

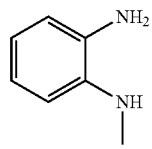
(II)

and 2-propyl-4-methyl-1H-benzimidazole-6-carboxylic acid of formula (III) or the salts thereof

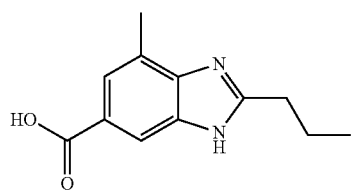
(III)

are reacted in the presence of phosphorus pentoxide in methanesulphonic acid to obtain 1,7'-dimethyl-2'-propyl-2,5'-bi-1H-benzimidazole, the individual reaction components being used in the following order and in the following temperature ranges:

phosphorus pentoxide is placed in methanesulphonic acid. Then 2-propyl-4-methyl-1H-benzimidazole-6-carboxylic acid is metered in, followed by N-methyl-o-phenylene-diamine in methanesulphonic acid, at a maximum temperature of 150° C.

The present invention relates to an alternative process for preparing 1,7'-dimethyl-2'-propyl-2,5'-bi-1H-benzimidazole of formula (I)

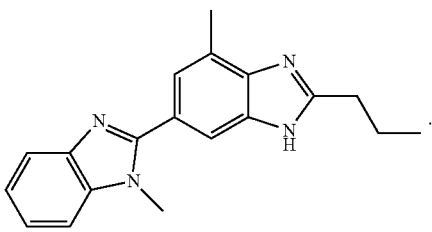
(I)

In this process N-methyl-o-phenylene-diamine of formula (II) or the salts thereof

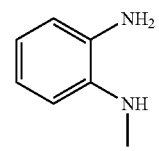
(II)

is/are reacted with 2-propyl-4-methyl-1H-benzimidazole-6-carboxylic acid of formula (III) or the salts thereof

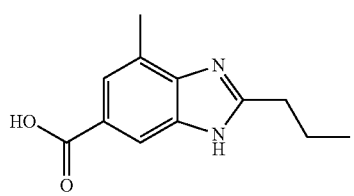
(III)

wherein
(a) the compound of formula (III) or one of the salts thereof is dissolved in a polar solvent,
(b) the compound of formula (II) or one of the salts thereof is added to this solution,
(c) then phosphorus pentoxide is added to this mixture of the two starting compounds in a polar solvent, and
(d) the reaction is carried out in a temperature range of up to 160° C., preferably at 110-160° C.

Besides the compound of formula (II) its salts may also be used in this process. The preferred salts are the phosphate, perchlorate, chlorine or bromine salt. The phosphate salt is particularly preferred. The latter can be described by the formula

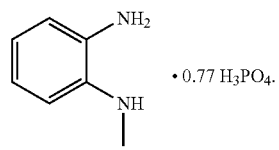

Analogously, instead of the 2-propyl-4-methyl-1H-benzimidazole-6-carboxylic acid of formula (III), it is also possible to use the salts thereof. Preferred salts are the salts with sodium or potassium. Particularly preferred is the free carboxylic acid.

Thus, for example, (a) solvent is taken,
(b) 2-propyl-4-methyl-1H-benzimidazole-6-carboxylic acid of formula (III) is added, preferably over a period of at least 15 minutes,
(c) N-methyl-o-phenylene-diamine of formula (II) is added, preferably over a period of at least 15 minutes,
(d) phosphorus pentoxide is added, preferably over a period of at least 15 minutes,
(e) the mixture is kept for at least 1 hour at a maximum temperature of 160° C., preferably at 130° C. to 160° C.,
(f) then the mixture is preferably diluted while cooling with water and is adjusted with base to a pH of 0-3, treated with charcoal and finally
(g) the product 1,7'-dimethyl-2'-propyl-2,5'-bi-1H-benzimidazole is extracted with a solvent such as isopropanol, and isolated after the addition of an antisolvent such as water.

Suitable solvents for use in step (a) of this process include polar solvents such as N,N-dimethylformamide, N,N-dimethylacetamide, dimethylsulphoxide, sulphonic acid derivatives such as methanesulphonic acid, methanol, ethanol and 2-propanol, preferably methanol, ethanol and methanesulphonic acid.

Suitable solvents for the extraction in step (g) include higher-order alcohols such as isopropanol as well as solvents that are immiscible with water as the antisolvent.

Steps (a) and (b) are preferably carried out in a temperature range of from 50° C. to 160° C., particularly preferably at 75° C. to 85° C.

Step (c) is preferably carried out in a temperature range of from 50° C. to 160° C., particularly preferably at 85° C. to 95° C.

Step (d) is preferably carried out in a temperature range of not more than 160° C., particularly preferably at 110° C. to 130° C.

The compound obtained, 1,7'-dimethyl-2'-propyl-2,5'-bi-1H-benzimidazole, is purified by treating the product with charcoal, extracting it in 2-propanol and isolating it from isopropanol/water. The purity level of more than 98% is determined by HPLC measurement and is between 99% and 100%, preferably 99.5%. Compared with the conventional method, this therefore results in an improvement of a factor of two in relation to the sum of the impurities.

The preparation of 1,7'-dimethyl-2'-propyl-2,5'-bi-1H-benzimidazole using the method described is more efficient, as yields of more than 80%, preferably more than 85%, can be isolated and the product purity significantly exceeds that of the conventional process.

The invention further relates to 1,7'-dimethyl-2'-propyl-2, 5'-bi-1H-benzimidazole of formula (I) prepared by the process described, which is suitable for preparing the pharmaceutical active substance telmisartan

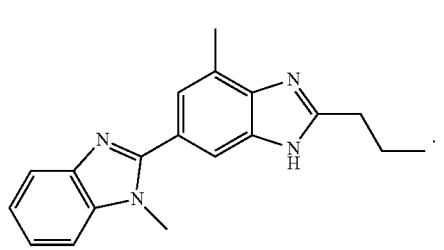

(I)

EXAMPLES

Example 1

Variant 1

Methanesulphonic acid is heated to a temperature of 115° C. to 130° C.

Phosphorus pentoxide is added at a maximum temperature of 145° C. 2-Propyl-4-methyl-1H-benzimidazole-6-carboxylic acid is added at about 130-135° C. Finally, N-methyl-o-phenylene-diamine is added at about 135° C. The mixture is then stirred for 3 hours at a maximum temperature of 145° C. It is cooled to <100° C. and water is metered into the reaction mixture. 50% sodium hydroxide solution is added at <100° C. until a pH of less than 3 is obtained. Finally, treatments with charcoal are carried out at <100° C.

At a temperature of <80° C. isopropanol is added and the mixture is adjusted with sodium hydroxide solution to a pH between 4.5 and 7. The aqueous phase is separated off. In order to precipitate dimethyl-2'-propyl-2,5'-bi-1H-benzimidazole water is metered in, the contents of the apparatus are cooled to at least 40° C. for technical reasons and the product is isolated.

Yield: 74-85% of theory
HPLC-purity: >99.5%.

Example 2

Variant 2

Methanesulphonic acid is heated to about 80° C. At a temperature of 75° C. to 85° C., 2-propyl-4-methyl-1H-benzimidazole-6-carboxylic acid is added. Then at 85° C. to 95° C. N-methyl-o-phenylene-diamine is added.

The mixture is heated to 110° C. to 130° C. and phosphorus pentoxide is metered in until an internal temperature of not more than 160° C. is reached. Then the mixture is stirred for 3 hours at a maximum temperature of 145° C. It is cooled to <100° C. and water is metered into the reaction mixture. 50% sodium hydroxide solution is added at <100° C. until a pH of less than 3 is obtained.

Finally, treatments with charcoal are carried out at <100° C.

At a temperature of <80° C. isopropanol is added and the mixture is adjusted with sodium hydroxide solution to a pH between 4.5 and 7. The aqueous phase is separated off. In order to precipitate dimethyl-2'-propyl-2,5'-bi-1H-benzimidazole water is metered in, the contents of the apparatus are cooled to at least 40° C. for technical reasons and the product is isolated.

Yield: 78-90% of theory
HPLC purity: >99.5%.

The invention claimed is:

1. A process for preparing 1,7'-dimethyl-2'-propyl-2,5'-bi-1H-benzimidazole of formula (I)

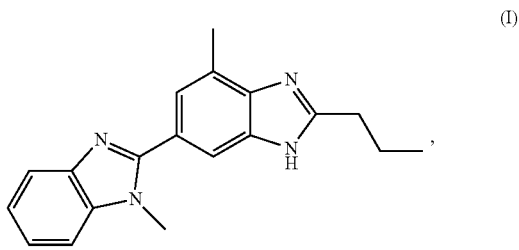 [SMILES: CCCc1nc2c(C)cc(-c3nc4ccccc4n3C)cc2[nH]1]

(I)

the process comprising reacting N-methyl-o-phenylene-diamine of formula (II) or a salt thereof

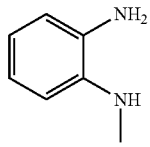
(II)

with 2-propyl-4-methyl-1H-benzimidazole-6-carboxylic acid of formula (III) or a salt thereof

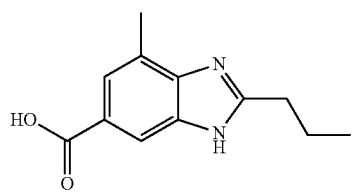
(III)

wherein:
(a) the compound of formula (III) or one of the salts thereof is dissolved in a polar solvent,
(b) the compound of formula (II) or one of the salts thereof is added to this solution,
(c) then phosphorus pentoxide is added to this mixture of the two starting compounds in a polar solvent, and
(d) the reaction is carried out in a temperature range of up to 160° C.

2. The process according to claim 1, wherein the salt of the compound of formula (II) is

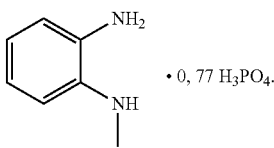
· 0, 77 H$_3$PO$_4$.

3. The process according to claim 1, wherein:
(a) 2-propyl-4-methyl-1H-benzimidazole-6-carboxylic acid of formula (III) is added to a polar solvent,
(b) N-methyl-o-phenylene-diamine of formula (II) is added to the mixture of the prior step,
(c) phosphorus pentoxide is added to the mixture of the prior step,
(d) the mixture of the prior step is kept at a maximum temperature of 160° C. for at least 1 hour,
(e) then the mixture of the prior step is diluted and adjusted to a pH of 0-3 with base, and
(f) the product 1,7'-dimethyl-2'-propyl-2,5'-bi-1H-benzimidazole is treated with charcoal, extracted with a solvent such as isopropanol, and isolated from isopropanol/water.

4. The process according to claim 1, wherein the polar solvent is N,N-dimethylformamide, N,N-dimethylacetamide, sulphonic acid derivatives, dimethylsulphoxide, methanol, ethanol, or 2-propanol.

5. The process according to claim 3, wherein the polar solvent is methanesulphonic acid.

6. The process according to claim 5, wherein:
step (a) is carried out at a temperature of 50° C. to 160° C.;
step (b) is carried out at a temperature of 50° C. to 160° C.;
step (c) is carried out at a temperature of 50° C. to 160° C.; and
step (d) is carried out at a temperature of not more than 160° C.

7. The process according to claim 1, wherein a yield of more than 80% is achieved.

8. The process according to claim 1, wherein the degree of purity of 1,7'-dimethyl-2'-propyl-2,5'-bi-1H-benzimidazole exceeds 98%.

9. The process according to claim 1, further comprising additional reactions to convert 1,7'-dimethyl-2'-propyl-2,5'-bi-1H-benzimidazole to obtain telmisartan.

10. The process according to claim 1, wherein the reaction is carried out in a temperature range of 110° C.-160° C.

11. The process according to claim 6, wherein:
step (a) is carried out at a temperature of 75° C. to 85° C.;
step (b) is carried out at a temperature of 75° C. to 85° C.;
step (c) is carried out at a temperature of 85° C. to 95° C.; and
step (d) is carried out at a temperature of 110° C. to 130° C.

* * * * *